United States Patent [19]

Breuer et al.

[11] 4,275,062
[45] Jun. 23, 1981

[54] AMINOTHIAZOLYL UREIDO SULFOXIDE CEPHALOSPORINS

[75] Inventors: Hermann Breuer; Theodore Denzel; Uwe D. Treuner, all of Regensburg, Fed. Rep. of Germany

[73] Assignee: E. R. Squibb & Sons, Inc., Princeton, N.J.

[21] Appl. No.: 77,056

[22] Filed: Sep. 19, 1979

[51] Int. Cl.³ .................. A61K 31/545; C07D 501/34
[52] U.S. Cl. .................................... 424/246; 544/21;
544/22; 544/23; 544/25; 544/27; 544/28
[58] Field of Search .................. 424/246; 544/27, 28, 544/21, 22, 23, 25

[56] References Cited

U.S. PATENT DOCUMENTS

| | | | |
|---|---|---|---|
| 3,673,183 | 6/1972 | Erickson | 424/246 |
| 3,708,479 | 1/1973 | Welch et al. | 424/246 |
| 3,833,568 | 9/1974 | Dolfini et al. | 424/246 |
| 3,860,591 | 1/1975 | Breuer | 424/246 |
| 3,971,778 | 7/1976 | Cook et al. | 424/246 |
| 3,978,051 | 8/1976 | Dolfini | 424/246 |
| 3,989,693 | 11/1976 | Dolfini | 424/246 |
| 3,989,697 | 11/1976 | Dolfini | 424/246 |
| 3,996,217 | 12/1976 | Breuer et al. | 424/246 |
| 3,996,218 | 12/1976 | Breuer et al. | 424/246 |
| 4,000,134 | 12/1976 | Dolfini | 424/246 |
| 4,024,135 | 5/1977 | Breuer et al. | 424/246 |
| 4,061,852 | 12/1977 | Dolfini | 544/27 |
| 4,075,337 | 2/1978 | Marx et al. | 424/246 |
| 4,088,815 | 5/1978 | Breuer et al. | 544/26 |
| 4,088,816 | 5/1978 | Treuner et al. | 544/27 |
| 4,098,888 | 7/1978 | Ochiai | 424/246 |
| 4,127,716 | 11/1978 | Breuer et al. | 544/27 |
| 4,138,555 | 2/1979 | Cook et al. | 544/22 |
| 4,152,432 | 5/1979 | Heymes | 424/246 |
| 4,237,128 | 12/1980 | Cimarusti et al. | 424/246 |

FOREIGN PATENT DOCUMENTS 2716677 10/1978 Fed. Rep. of Germany .

Primary Examiner—Paul M. Coughlan, Jr.
Attorney, Agent, or Firm—Lawrence S. Levinson; Dale Lovercheck

[57] ABSTRACT

Cephalosporins of the formula

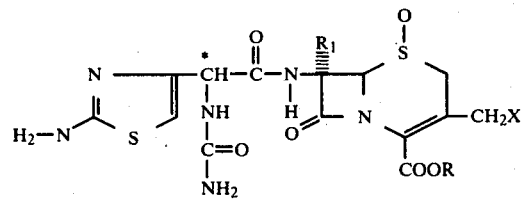

R represents hydrogen, sodium, potassium, or certain ester groups,
$R_1$ is in the α-configuration and is hydrogen or methoxy, X represents hydrogen

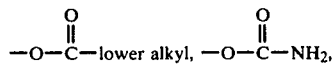

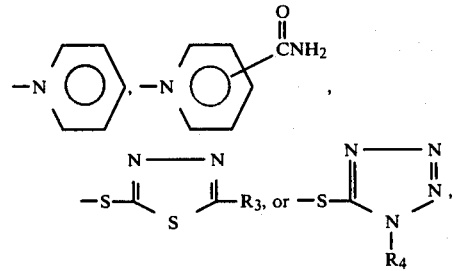

$R_3$ represents hydrogen or lower alkyl, $R_4$ is hydrogen, lower alkyl,

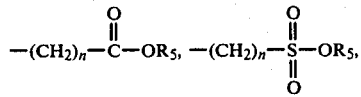

or $-(CH_2)_n-N-$(lower alkyl)$_2$, $R_5$ represents hydrogen, sodium or potassium, and n represents an integer from 1 to 4. These compounds are useful as antibacterial agents.

20 Claims, No Drawings

AMINOTHIAZOLYL UREIDO SULFOXIDE CEPHALOSPORINS

RELATED APPLICATIONS

The corresponding aminothiazolyl ureido cephalosporins are disclosed in copending application U.S. Ser. No. 046,068.

BACKGROUND OF THE INVENTION

Cephalosporins having a ureido substituted acyl sidechain and various groups in the 3-position are disclosed by Erickson in U.S. Pat. No. 3,673,183, Welch et al. in U.S. Pat. No. 3,708,479, Dolfini in U.S. Pat. No. 3,833,568, Breuer in U.S. Pat. No. 3,860,591, and Breuer et al. in U.S. Pat. Nos. 3,996,217, 3,996,218, 4,024,135, 4,088,815, 4,088,816, and 4,127,716.

Various 7α-methoxy cephalosporins having a ureido substituted acyl sidechain and various groups in the 3-position are disclosed by Dolfini in U.S. Pat. Nos. 3,978,051, 3,989,693, 3,989,697, 4,000,134 and 4,061,852.

Ochiai et al. in U.S. Pat. No. 4,098,888 disclose cephalosporins having an aminothiazolyl acetamido acyl sidechain with an amino, hydroxy, or imino group on the α-carbon atom of the acyl sidechain.

Heymes in U.S. Pat. No. 4,152,432 disclose cephalosporins having an aminothiazolyl acetamido acyl sidechain with an imino group on the α-carbon atom of the acyl sidechain.

Hoechst in German Offenlegungsschrift No. 2,716,677 discloses α- and β-sulfoxides of cephalosporins having an aminothiazolyl acetamido acyl sidechain with an imino group on the α-carbon atom of the acyl sidechain.

Marx et al. in U.S. Pat. No. 4,075,337 disclose the preparation of antibacterially active cephalosporin sulfoxides.

Cook et al. in U.S. Pat. Nos. 3,971,778 and 4,138,555 disclose the preparation of additional antibacterially active cephalosporin sulfoxides.

SUMMARY OF THE INVENTION

This invention is directed to the new cephalosporins of the formula

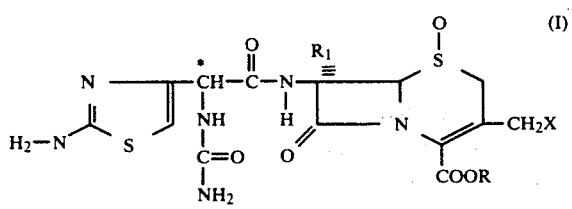

R represents hydrogen, sodium, potassium, t-butyl, benzyl, p-methoxybenzyl, p-nitrobenzyl, diphenylmethyl, 2,2,2-trichloroethyl, trimethylsilyl, —CH$_2$—O—lower alkyl,

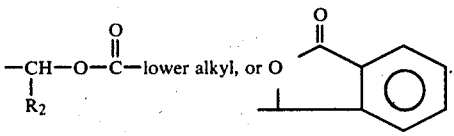

$R_1$ is in the α-configuration and is hydrogen or methoxy.

$R_2$ represents hydrogen or lower alkyl.

X represents hydrogen,

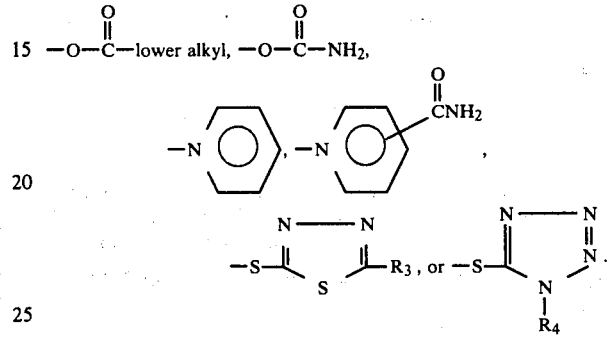

$R_3$ represents hydrogen or lower alkyl.
$R_4$ represents hydrogen, lower alkyl,

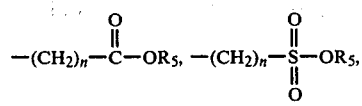

or —(CH$_2$)$_n$—N—(lower alkyl)$_2$.

$R_5$ represents hydrogen, sodium or potassium.

n represents an integer from 1 to 4.

When X is pyridinium or carbamoyl substituted pyridinium, the compounds can be structurally represented as having the formula

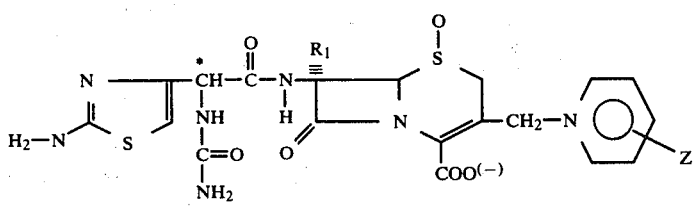

wherein Z is hydrogen or carbamoyl.

DETAILED DESCRIPTION OF THE INVENTION

The lower alkyl groups referred to throughout this specification include straight or branched chain hydrocarbon groups containing 1 to 4 carbons, e.g., methyl, ethyl, i-propyl, t-butyl, etc.

The compounds of formula I and the intermediates that are described below that include the 2-amino thiazolyl group as part of their structure are, of course, tautomeric and can also be structurally represented as a 2-imino group. Thus, for example, the compounds of formula I can be represented as

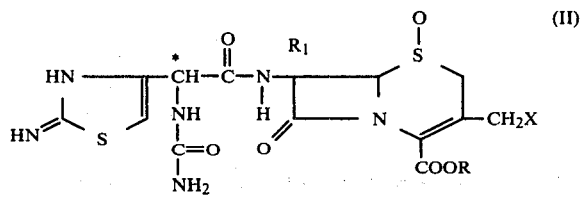 (II)

The intermediates and final products are being structurally represented and named throughtout this specification as 2-aminothiazoles though both forms are within the scope of the invention.

The symbol

is being used to represent that the sulfoxides of formula I and in the various intermediates described below can be in either the α- or β- configuration. When the sulfoxide is only in the β- configuration it will be represented as

and when it is only in the α-configuration it will be represented as

The compounds of formula I wherein the sulfoxide is in either the α- or β- configuration can be prepared by several methods. For example, the compounds of formula I wherein X is hydrogen,

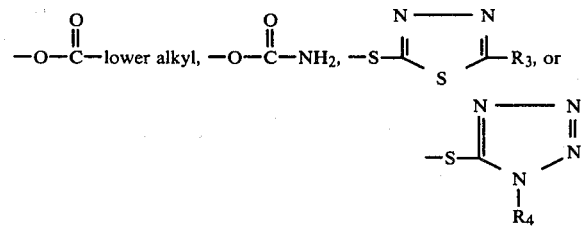

can be prepared by acylating an 7β-amino-7α-methoxy or desmethoxy cephalosporanic acid ester of the formula

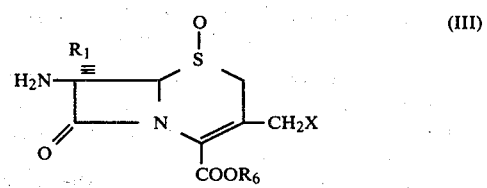 (III)

wherein $R_6$ is t-butyl, benzyl, p-methoxybenzyl, p-nitrobenzyl, diphenylmethyl, trimethylsilyl, lower alkoxymethyl, or 2,2,2-trichloroethyl, especially diphenylmethyl, with an activated derivative of the formula

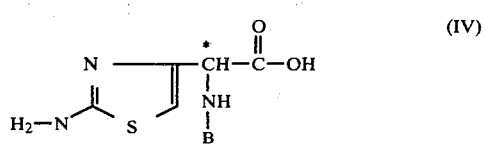 (IV)

wherein B is a protecting group such as

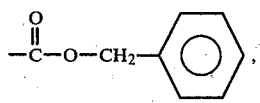,

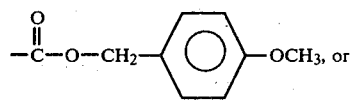, or $$-\overset{O}{\underset{\|}{C}}-O-C(CH_3)_3,$$

to yield the intermediate of the formula

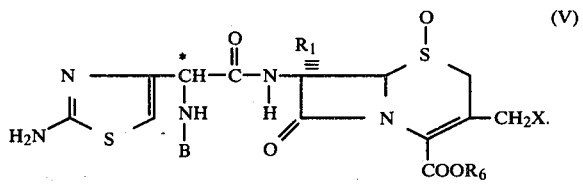 (V)

Suitable activated derivatives of the compound of formula IV are the acid chloride or bromide, an anhydride or mixed anhydride, or an activated ester formed according to methods known in the art. Alternatively, the reaction is performed directly with the acid of formula IV by use of coupling agents. The preferred coupling agents are N-hydroxybenzotriazole and dicyclohexylcarbodiimide.

The intermediate of formula V is then treated with trifluoroacetic acid and anisole to yield the α-amino cephalosporin of the formula

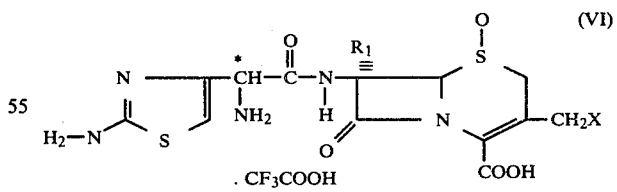 (VI)

Treatment of the trifluoroacetic acid salt of formula VI with potassium or sodium cyanate yields the compounds of formula I.

The 7-amino cephalosporanic acid ester α- and β-sulfoxides of formula III are prepared by converting the 7-amino cephalosporanic acid starting material to the Schiff base ester of the formula

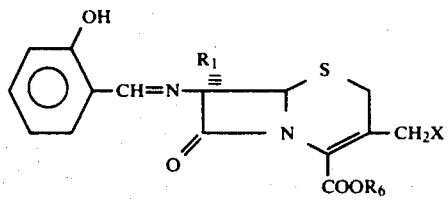

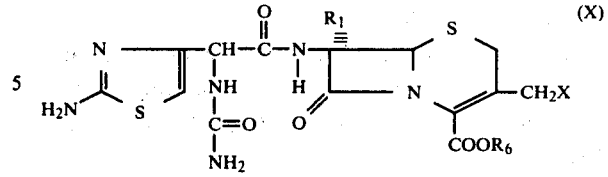

which is then oxidized with a percarboxylic acid such as m-chloroperbenzoic acid to yield a mixture of α- and β-sulfoxide Schiff base cephalosporin esters. The Schiff base sidechain is cleaved by treatment with toluenesulfonic acid and the α- and β-sulfoxide 7-amino cephalosporanic acid esters are separated chromatographically.

The compounds of formula Ia can be prepared by reacting a compound of formula I wherein R is hydrogen and X is

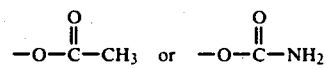

with pyridine or carbamoyl substituted pyridine in a polar solvent such as water and in the presence of a catalyst such as an alkali metal thiocyanate according to the procedures taught in U.S. Pat. No. 3,792,047 and German Offenlegungsschrift No. 2,234,280.

Also, the compounds of formula I wherein X is heterothio (i.e.

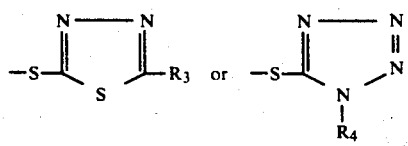

can be prepared by reacting the compound of formula I wherein R is hydrogen and X is

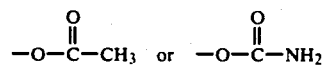

with a mercaptan of the formula (VIII) hetero-S—H or an alkali metal (preferably sodium) mercaptan salt of the formula (IX) hetero-S-alkali metal.

Such methods of introducing a heterothio group in the 3-position are disclosed in various U.S. Pat. Nos. including 3,855,213; 4,066,762; etc.

Also, the β-sulfoxides of formula I can be prepared by the direct oxidation of the corresponding sulfide compound. Thus, a cephalosporin of the formula wherein X, $R_1$, and $R_6$ are as defined above; is oxidized with a percaboxylic acid such as m-chloroperbenzoic acid, peracetic acid, etc., at from about 0° to about 25° C.

The sulfides of formula X are described in copending application U.S. Ser. No. 46,068 filed June 6, 1979. Also, the intermediates of formula IV are described in this application.

The compounds of formula I wherein R is sodium or potassium are prepared by reacting the corresponding free acid of formula I (R is hydrogen) with the appropriate salt forming ion.

The compounds of formula I wherein R is

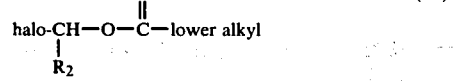

can be obtained by treating the corresponding free acid of formula I with one or two moles of a compound of the formula

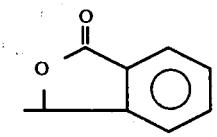

wherein halo is chlorine or bromine in an inert solvent such as dimethylformamide at or below ambient temperature.

Similarly, the compounds of formula I wherein R is are prepared by treating the free acid compound of formula I with a compound of the formula

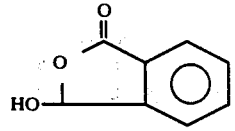

as taught by Ferres et al. in U.S. Pat. No. 3,860,579.

The symbol C in the preceding formulas represents an asymmetric carbon atom. By selection of the appropriate starting materials, it is possible to obtain the compounds of formula I as a mixture of optically active isomers or isolated as a single isomer. Also, when the final product is obtained in the D,L-form, the pure D- and L-diastereoisomers can be obtained by preparative high performance liquid chromatography (HPLC). The various isomers as well as their mixtures are within the scope of this invention.

Preferred compounds of this invention as final products are the β-sulfoxides of formula I wherein R is hydrogen, sodium or potassium; $R_1$ is hydrogen; X is hydrogen,

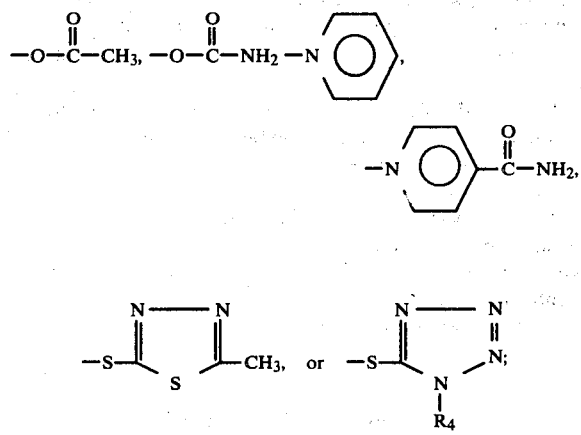

$R_4$ is hydrogen, methyl, —CH$_2$COOR$_5$,

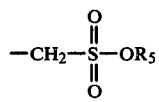

or —(CH$_2$)$_2$—N(CH$_3$)$_2$; and $R_5$ is hydrogen, sodium or potassium.

Most preferred as final products are the above compounds wherein X is

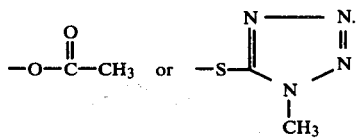

Also preferred as intermediates are the β-sulfoxides of formula VI wherein $R_1$ is hydrogen and X is hydrogen,

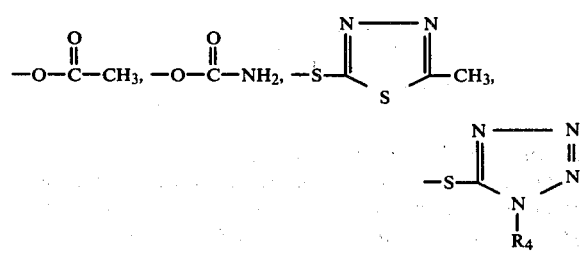

and $R_4$ is defined as above.

Most preferred as intermediates are the above compounds wherein X is

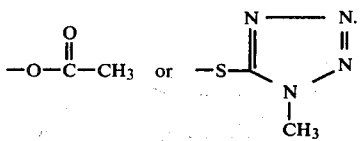

The compounds of formula I wherein R is hydrogen, sodium, potassium, —CH$_2$—O—lower alkyl,

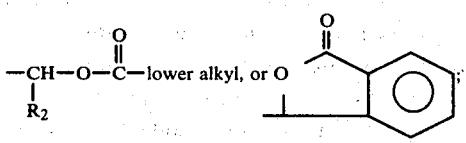

are useful antibacterial agents possessing activity against various gram positive and gram negative organisms such as *Escherichia coli, Enterobacter cloacae, Klebsiella pneumoniae, Klebsiella aerogenes, Proteus rettgeri, Proteus vulgarius, Proteus mirabilis, Serratia marcescens, Salmonella typhimurium, Shigella sonnei, Citrobacter freundii*, etc.

The active final products may be used as antibacterial agents to combat infections due to organisms such as those named above, and in general may be utilized in a manner similar to cephalothin and other cephalosporins. For example, a compound of formula I or a phsyiologically acceptable salt or ester thereof may be used in various animal species in an amount of about 1 to 100 mg./kg., daily, parenterally, in single or two to four divided doses to treat infections of bacterial origin, e.g., 5.0 mg./kg. in mice.

Up to about 600 mg. of an acid compound of formula I or a physiologically acceptable salt or ester thereof may be incorporated in an injectable form in a sterile aqueous vehicle prepared according to conventional pharmaceutical practice.

Illustrative process details are provided in the Examples for the various reactions. All temperatures are on the centigrade scale.

EXAMPLE 1

[5S-[5α,6β,7α(±)]]-3-[(Acetyloxy)methyl]-7-[[[(aminocarbonyl)amino]
(2-amino-4-thiazolyl)acetyl]amino]-8-oxo-5-thia-1-azabicyclo[4.2.0]oct-2-ene-2-carboxylic acid, 5-oxide, sodium salt (i.e. β-sulfoxide)

(a)

[5S-[5α,6β,7α]]-3-[(Acetyloxy)methyl]-7-amino-8-oxo-5-thia-1-azabicyclo[4.2.0]oct-2-ene-2-carboxylic acid, 5-oxide, diphenylmethyl ester (i.e. β-sulfoxide) and [5R-[5α,6α,7β]]-3-[(Acetyloxy methyl]-7-amino-8-oxo-5-thia-1-azabicyclo[4.2.0]oct-2-ene-2-carboxylic acid, 5-oxide, diphenylmethyl ester (i.e. α-sulfoxide)

A slurry of 50 g. of 7-aminocephalosporanic acid (7-ACA) in 1 liter of water is stirred magnetically while t-octyl amine is added dropwise, thereby maintaining the pH between 7 and 8. After one hour, the undissolved solid is filtered (Celite) and the filtrate is treated with a solution prepared by adjusting a mixture of 10 ml. of t-octylamine and 20 ml. of water to pH 8.0 with 6 N hydrochloric acid. The resulting solution is then treated with 10 ml. of salicylaldehyde. After 2 minutes a solid forms and after 5 minutes an additional 10 ml. of salicylaldehyde is added. The slurry is stirred for an additional 10 minutes, cooled to 0° for 4.5 hours and filtered. The filter cake is slurried twice with 300 ml. of cold water and filtered. The wet cake is dried at 60° in vacuo over large amounts of $P_2O_5$ to give 66 g. of tan solid 7-salicylaldiminocephalosporanic acid, t-octyl amine salt.

A slurry of 25.25 g. (0.05 mole) of the above t-octyl amine salt (powdered with a mortar and pestle) in 250 ml. of dry acetonitrile is treated with 9.5 g. (0.05 mole) of p-toluenesulfonic acid monohydrate. After 10 minutes, a solution of 9.7 g. (0.05 mole) of diphenyldiazomethane in 50 ml. of acetonitrile is added over the course of 15 minutes. After one hour, the slurry is filtered, the solid is washed with acetonitrile, and the combined filtrate and washings are evaporated in vacuo. The resulting oil is chromatographed on a 300 g. silica gel column eluted with methylene chloride. Fractions (500 ml.) 2-3 contain 7.5 g. of the desired diphenylmethyl ester product plus some higher $R_f$ impurity (monitored by silica gel TLC with 3:1 chloroformethyl acetate development): fractions 4-11 contain 12.3 g. of pure 7-salicylaldiminiocephalosporanic acid, diphenylmethyl ester; NMR (CDCl$_3$) $\delta$1.97 (s, 3H, CH$_3$CO); 3.23 and 3.60 (AB q, J=19 Hz, 2H, C-2); 4.67 and 5.01 (AB q, J=14 Hz, 2H, C-3'); 4.99 (d, J=5 Hz, 1H, C-6); 5.20 (broadened d, J=5 Hz, 1H, C-7); 6.62-7.60 (m, about 15H); 9.07 (broad s, 1H, —CH=N—).

A solution of 12.3 g (0.023 mole) of the above diphenylmethyl ester product in 125 ml. of methylene chloride is cooled to 0° and a solution of 4.6 g. (0.023 mole) of 85% m-chloroperbenzoic acid in 70 ml. of methylene chloride is added over the course of 15 minutes. After one hour, the slurry is washed with a mixture of 100 ml. of 5% sodium bicarbonate and 50 ml. of 6% sodium sulfite solution. The organic layer is dried and evaporated in vacuo. The resulting oil crystallizes from 70 ml. of ethyl acetate giving 8.7 g. of a mixture of $\alpha$- and $\beta$-sulfoxides. A second crop of 1.5 g. of a mixture of $\alpha$- and $\beta$-sulfoxides is also obtained. The major ($\alpha$-) isomer has a lower field acetate methyl (2.02 ppm) and C-2 quartet (3.57 and 4.10 ppm) when compared to those of the minor ($\beta$) isomer (1.97, 3.26 and 3.94 ppm, respectively).

A slurry of 10 g. (0.018 mole) of the above 7 salicylaldimiocephalosporanic acid, diphenylmethylester, $\alpha$- and $\beta$-sulfoxide mixture in 100 ml. of ethyl acetate is treated with 3.42 g. (0.018 mole) of p-toluenesulfonic acid monohydrate. After 5.5 hours, 300 ml. of ether is added and the gummy solid is triturated, filtered, and washed twice with ether. The moist solid is dissolved in 200 ml. of ethyl acetate and the solution is washed with 100 ml. of 5% sodium bicarbonate solution, dried, and evaporated to give 8.0 g. of residue. Chromatography on a 300 g. silica gel column eluted with 3:1 chloroformethyl acetate gives (500 ml. fractions): fraction 3, 1.0 g. of recovered 7-salicylaldiminocephalosporanic acid, diphenylmethyl ester; fractions 6-16, 4.5 g. of [5R-[5$\alpha$,-6$\alpha$,7$\beta$[[-3-[(acetyloxy)methyl]-7-amino-8-oxo-5-thia-1-azabicyclo[4.2.0]oct-2-ene-2-carboxylic acid, 5-oxide, diphenyl ester (i.e., $\alpha$-sulfoxide isomer): NMR (CDCl$_3$) $\delta$ 2.00 (CH$_3$COO—); 3.43 and 4.06 ppm (AB q, C-2); fraction 22 30 (eluant is changed to ethyl acetate after fraction 16) 1.5 g. of [5S-[5$\alpha$,6$\beta$,7$\alpha$]]-3-[(acetyloxy)methyl]-7-amino-8-oxo-5-thia-1-azabicyclo[4.2.0]oct-2-ene-2-carboxylic acid, 5-oxide, diphenylmethyl ester (i.e., $\beta$-sulfoxide isomer): NMR (CDCl$_3$) $\delta$ 2.10 (CH$_3$COO—); 2.97 and 3,54 ppm (AB q, C-2).

(b)
[5S-[5$\alpha$,6$\beta$,7$\alpha$($\pm$)[-3-[(Acetyloxy)methyl]-7-[[[[(4-methoxyphenyl)methoxy]carbonyl]amino] (2-amino-4-thiazolyl)acetyl]amino[-8-oxo-5-thia-1-azabicyclo[4.2.0]oct-2-ene-2-carboxylic acid, 5-oxidediphenylmethyl ester (i.e. $\beta$-sulfoxide)

A solution of 4.1 g. (0.012 mole) of D,L-2-amino-$\alpha$-[[[(4-methoxyphenyl)methoxy]carbonyl]amino]-4-thiazoleacetic acid, 4.54 g. (0.01 mole) of the $\beta$-sulfoxide diphenylmethyl ester from part (a), and 1.6 g. (0.01 mole) of N-hydrobenzotriazole in a mixture of 60 ml. of dimethylformamide and 60 ml. of acetonitrile and 5 g. of molecular sieve is stirred for 30 minutes and then cooled to 0°-5°. 2.27 g. (0.011 mole) of dicyclohexylcarbodiimide in 20 ml. of dimethylformamide is added dropwise over 30 minutes. Stirring is continued for 90 minutes at 0° and 90 minutes at room temperature. Dicyclohexylurea is filtered off and the filtrate is diluted with ethyl acetate, and then washed with water. The resulting crystals are filtered off to yield 3.5 g. of [5S-[5$\alpha$;6$\beta$,7$\alpha$($\pm$)-3-[(acetyloxyloxy)methyl]-7-[[[[[(4-methoxyphenyl)methoxy]carbonyl]amino] (2-amino-4-thiazolyl)acetyl]amino]-8-oxo-5-thia-1-azabicyclo[4.2.-0]oct-2-ene-2-carboxylic acid, 5-oxide, diphenylmethyl ester; m.p. 168°-170° (dec.). An additional 2.3 g. of product can be obtained by reworking the ethyl acetate phase.

(c)
[5S-[5$\alpha$,6$\beta$,7$\alpha$(35)]]-3-[(acetyloxy)methyl]-7-[[amino(2-amino-4-thiazolyl)acetyl]amino]-8-oxo-5-thia-1-azabicyclo[4.2.0]oct-2-ene-2-carboxylic acid, trifluoroacetate salt (i.e. $\beta$-sulfoxide)

3.2 g. of the diphenylmethyl ester product from part (b) is added to 11 ml. of anisole. The mixture is cooled to 0° and 27 ml. of trifluoroacetic acid is added and the solution is stirred for 15 minutes. Excess trifluoroacetic acid is removed in vacuo and the residue is treated with ether to yield 2.3 g. of [5S-[5$\alpha$,6$\beta$,7$\alpha$($\pm$)]]-3-[(acetyloxy)methyl]7-[[amino(2-amino-4-thiazolyl)acetyl]amino]-8-oxo-5-thia-1-azabicyclo[4.2.0]oct-2-ene-2-carboxylic acid, trifluoroacetate salt; m.p. 140°-220° (resinous melting).

(d)
[5S-[5$\alpha$,6$\beta$,7$\alpha$($\pm$)]]-3-[(acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt (i.e. $\beta$-sulfoxide)

0.52 g. of sodium cyanate is added to a suspension of 2.2 g. of the trifluoroacetic acid salt product from part (c) in 16 ml. of water. The reaction mixture is stirred for three hours at room temperature. The slightly cloudy solution is filtered and the clear solution is purified by treatment with the ion exchange resin Amberlite XAD-2. Elution is carried out with water. The desired product is contained in fractions 25-80. These fractions are combined and lyophilized and the residue X is triturated with ether to yield 1.3 g. of [5S-[5$\alpha$,6$\beta$,7$\alpha$($\pm$)]]-3-[(acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt; m.p. greater than 330°.

EXAMPLE 2

[5R-[5α,6α,7β(±)]]-3-[(Acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt (i.e. α-sulfoxide)

Following the procedure of Example 1 parts (b) to (d) but employing the α-sulfoxide diphenylmethyl ester from part (a) in place of the β-sulfoxide, one obtains [5R-[5α,6α,7β(±)]]-3-[(acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt.

EXAMPLE 3

[5S-[5α,6β,7α(±)]]-7-[[[(Aminocarbonyl)amino]-(2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, sodium salt (i.e. β-sulfoxide)

(a)

[5S-[5α,6β,7α]]-7-amino-3-[[(1-methyl-1H-tetrazol-5-yl)thio]methyl]-8-oxo-5-thia-1-azabicyclo[4.2.0]oct-2-ene-2-carboxylic acid, 5-oxide, diphenylmethyl ester (i.e. β-sulfoxide) and
[5R-[5α,6α,7β]]-7-amino-3-[[(1-methyl-1H-tetrazol-5-yl)thio]methyl]-8-oxo-5-thia-1-azabicyclo[4.2.0]oct-2-ene-2-carboxylic acid, 5-oxide, diphenylmethyl ester (i.e. α-sulfoxide)

Following the procedure of Example 1(a) but substituting 7-amino-3-[[(1-methyl-1H-tetrazol-5-yl)thio]methyl]-8-oxo-5-thia-1-azabicyclo[4.2.0]oct-2-ene-2-carboxylic acid for the 7-ACA one obtains a mixture of the desired sulfoxide products which are then separated chromatographically to yield the individual α- and β-sulfoxides.

(b)

[5S-[5α,6β,7α(±)]]-7-[[[[(4-methoxyphenyl)methoxy]carbonyl]amino](2-amino-4-thiazolyl)acetyl]amino]-3-[[(1-methyl-1H-tetrazol-5-yl)thio]methyl]8-oxo-5-thia-1-azabicyclo[4.2.0]oct-2-ene-2-carboxylic acid, 5 oxide, diphenylmethyl ester (i.e. β-sulfoxide)

Following the procedure of 1(b) but employing the β-sulfoxide diphenylmethyl ester from Example 3(a) one obtains the desired product. Crystallization from ethyl acetate yields [5S-[5α,6β,7α(±)]]-7-[[[[(4-methoxyphenyl)methoxy]carbonyl]amino](2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, diphenylmethyl ester; m.p. 166°-169° (dec.)

(c)

[5S-[5α,6β,7α(±)]]-7-[[Amino(2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, trifluoroacetate salt (1:1). (i.e. β-sulfoxide)

Following the procedure of Example 1(c), the β-sulfoxide dimethylester product (2.8 g.) is treated with trifluoroacetic acid and anisole to yield 2 g. of [5S-[5α,6β,7α(±)]]-7-[[amino(2-amino-4-thiazolyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, 5-oxide, trifluoroacetate salt (1:1); m.p. 140°-220° (resinous melting).

(d)

[5S-[5α,6β,7α(±)]]-7-[[[(Aminocarbonyl)amino](2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, sodium salt (i.e. β-sulfoxide)

0.42 g sodium cyante is added to 2.0 g. of trifluoroacetic acid salt product from example 3(c) in 13 ml. of water. This reaction mixture is stirred for three hours at room temperature. The slightly cloudy solution is filtered and the clear solution is purified by treatment with the ion exchange resin Amberlite XAD-2. The ion exchange column is eluted with a mixture of 20 percent methanol and 80 percent water. The desired product is contained in fractions 25-80. These fractions are combined and lyophilized and the residue is triturated with ether to yield 10 g. of [5S-[5α,6β,7α(±)]]-7-[[[(Aminocarbonyl)amino]-(2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, sodium salt.

The product melting point is greater than 320° (resinous melting at 320°).

EXAMPLE 4

[5S-[5α,6β,7α(±)]]-3-[(Acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt. (i.e. α-sulfoxide)

Following the procedure of Example 3 parts (b) to (d) but employing the α-sulfoxide diphenylmethyl ester from part (a) (of Example 3) in place of the β-sulfoxide, one obtains [5S-[5α,6β,7α(±)]]-3-[(Acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide, sodium salt. (i.e. α-sulfoxide)

EXAMPLES 5-16

Following the procedure of Examples 1 to 4 but employing the 7-aminocephalosporanic acid ester shown in Col. I and the 2-amino-4-thiazole acetic acid shown in Col. II one obtains after removal of the α-amino and carboxylic acid protecting group the trifluoroacetic acid salt shown in Col. III. Treatment with sodium cyanate yields the desired product shown in Col. IV.

Col. I

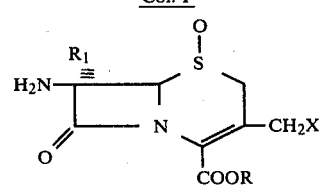

Col. II

-continued

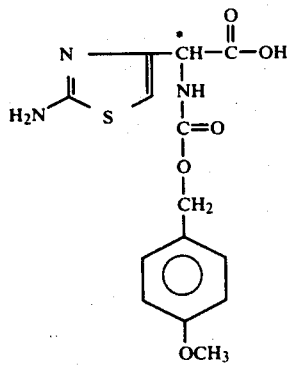

Col. III

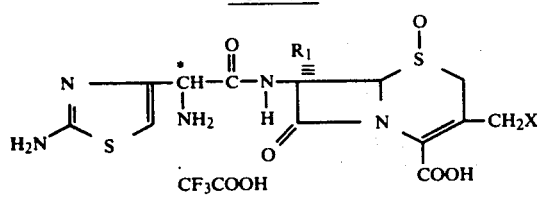

Col. IV

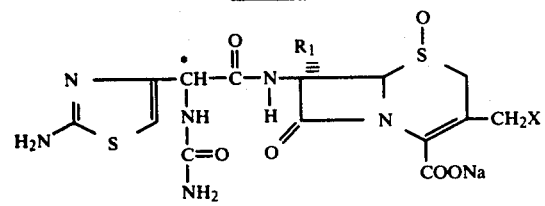

| Ex. | $R_1$ | R | X |
|---|---|---|---|
| 5 | —OCH$_3$ | —CH(—C$_6$H$_5$)$_2$ | —O—C(=O)—CH$_3$ |
| 6 | —OCH$_3$ | —CH(—C$_6$H$_5$)$_2$ | —S-(tetrazolyl-N-CH$_3$) |
| 7 | —H | —CH(—C$_6$H$_5$)$_2$ | —O—C(=O)—NH$_2$ |
| 8 | —OCH$_3$ | —CH(—C$_6$H$_5$)$_2$ | —O—C(=O)—NH$_2$ |
| 9 | —H | —CH(—C$_6$H$_5$)$_2$ | —H |
| 10 | —H | —CH(—C$_6$H$_5$)$_2$ | —S-(thiadiazolyl-CH$_3$) |
| 11 | —OCH$_3$ | —CH(—C$_6$H$_5$)$_2$ | —S-(thiadiazolyl-CH$_3$) |
| 12 | —H | —CH(—C$_6$H$_5$)$_2$ | —S-(triazolyl-NH) |
| 13 | —OCH$_3$ | —CH(—C$_6$H$_5$)$_2$ | —S-(triazolyl-N-C$_2$H$_5$) |

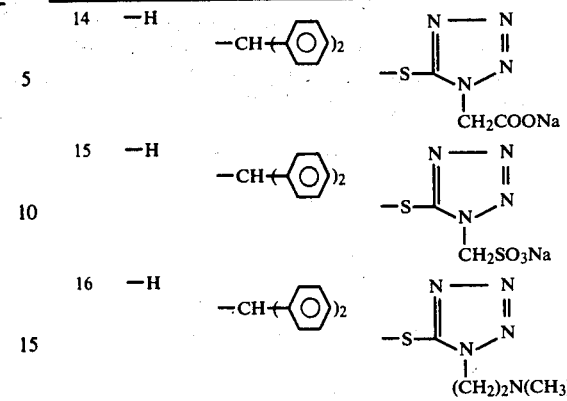

| 14 | —H | —CH(—C$_6$H$_5$)$_2$ | —S-(triazolyl-N-CH$_2$COONa) |
| 15 | —H | —CH(—C$_6$H$_5$)$_2$ | —S-(triazolyl-N-CH$_2$SO$_3$Na) |
| 16 | —H | —CH(—C$_6$H$_5$)$_2$ | —S-(triazolyl-N-(CH$_2$)$_2$N(CH$_3$)$_2$) |

The configuration of the sulfoxide group in the products of Examples 5 to 16 depends upon the configuration of the sulfoxide starting material shown in Col. I.

The products of Examples 5 to 16 are obtained as the D-, L- or the D,L-mixture depending upon the optical activity of the 2-amino-4-thiazole acetic acid shown in Col. II. Similarly, the products of Examples 1 to 4 could be obtained as the D- or L-isomer by employing the resolved 2-amino-4-thiazole acetic acid.

The products of Examples 1 to 16 can be converted into an ester form (i.e. R is

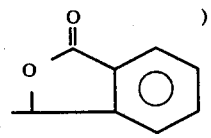

)

by reacting the acid product (i.e. R is hydrogen) according to known methods.

EXAMPLE 17

[5S-[5α,6β,7α(±)]]-7-[[[(aminocarbonyl)amino](2-amino-4-thiazolyl)acetyl]amino]-3-[[4-(aminocarbonyl)-pyridino]methyl]-8-oxo-5-thia-1-azabicyclo[4.2.0]oct-2-ene-2-carboxylic acid, 5-oxide (i.e. β-sulfoxide)

A mixture of 0.005 mole of the sodium salt product of Example 1, 0.0075 mole of 4-pyridinecarboxamide, 12 g. of potassium thiocyanate, and 7.5 ml. of water are heated at 50° for 24 hours. The resulting solution is passed through a chromatography column filled with 150 g. of ion exchanger Amberlite XAD-2. The column is washed with about 3 liters of water and the titled compound is eluted with a mixture of water:methanol (8:2). The methanol is evaporated from the eluate and the aqueous solution is lyophilized. The amorphous residue is triturated with ether and filtered under suction to yield [5S-[5α,6β,7α(±)]]-7-[[[(aminocarbonyl)amino](2-amino-4-thiazolyl)acetyl]amino]-3-[[4-(aminocarbonyl)pyridino]methyl]-8-oxo-5-thia-1-azabicyclo[4.2.0]oct-2-ene-2-carboxylic acid, 5-oxide.

Similarly, by employing the sodium salt product of Example 2 in the above procedure one obtains, [5R-[5α,6α,7β(±)]]-7-[[[(aminocarbonyl)amino](2-amino-4-thiazolyl)acetyl]amino]-3-[[4-(aminocarbonyl)-pyridino]methyl]-8-oxo-5-thia-1-azabicyclo[4.2.0]oct-2-ene-2-carboxylic acid, 5-oxide.

EXAMPLES 18–25

Following the procedure of Example 17 but employing the cephalosporanic acid sodium salt shown in Col. I and the pyridine compound shown in Col. II, one obtains the product shown in Col. III.

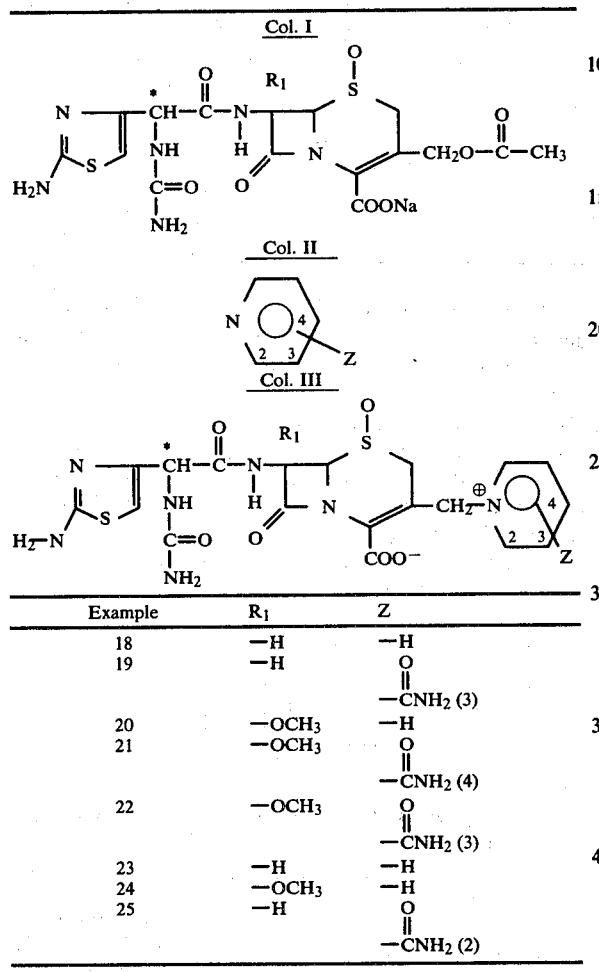

| Example | $R_1$ | Z |
|---|---|---|
| 18 | —H | —H |
| 19 | —H | —CNH$_2$ (3) (O) |
| 20 | —OCH$_3$ | —H |
| 21 | —OCH$_3$ | —CNH$_2$ (4) (O) |
| 22 | —OCH$_3$ | —CNH$_2$ (3) (O) |
| 23 | —H | —H |
| 24 | —OCH$_3$ | —H |
| 25 | —H | —CNH$_2$ (2) (O) |

The final products of Examples 18–25 are obtained in the D-, L-, or D,L-isomeric form depending upon the isomeric form of the cephalosporin shown in Col. I.

The configuration of the sulfoxide group in the products of Examples 18 to 25 depends upon the configuration of the sulfoxide starting material shown in Col. I.

EXAMPLE 26

[5S-[5α,6β,7α(±)]]-7-[[[(aminocarbonyl)amino](2-amino-4-thiazolyl)acetyl]amino]-3-[[(2-methyl-1,3,4-thiadiazol-5-yl)thio]methyl]-8-oxo-5-thia-1-azabicyclo[4.2.0]-oct-2-ene-2-carboxylic acid, 5-oxide, sodium salt (i.e. β-sulfoxide)

0.002 mol. of the sodium salt product of Example 1 is brought into solution in 100 ml. of a phosphate buffer at a pH of 6.4. Then 0.0024 mol. of 5-methyl-1,3,4-thiadiazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield [5S-[5α,6β,7α(±)]]-7-[[[(aminocarbonyl)amino](2-amino-4-thiazolyl)acetyl]amino]3-[[(2-methyl-1,3,4-thiadiazol-5-yl)thio]methyl]-8-oxo-5-thia-1-azabicyclo[4.2.0]oct-2-ene-2-carboxylic acid, 5-oxide, sodium salt.

Similarly, by employing the sodium salt product of Example 2 in the above procedure one obtains, [5R-[5α,6α,7β(±)]]-7-[[[(aminocarbonyl)amino](2-amino-4-thiazolyl)acetyl]amino]-3-[[(2-methyl-1,3,4-thiadiazol-5-yl)thio]methyl]-8-oxo-5-thia-1-azabicyclo[4.2.0]oct-2-ene-2-carboxylic acid, 5-oxide, sodium salt.

EXAMPLES 27–34

Following the procedure of Example 26 but employing the cephalosporanic acid sodium salt shown in Col. I and the thiol shown in Col. II, one obtains the product shown in Col. III.

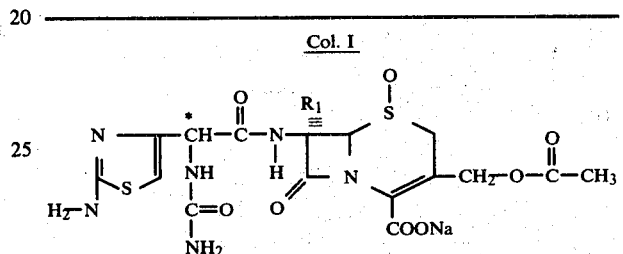

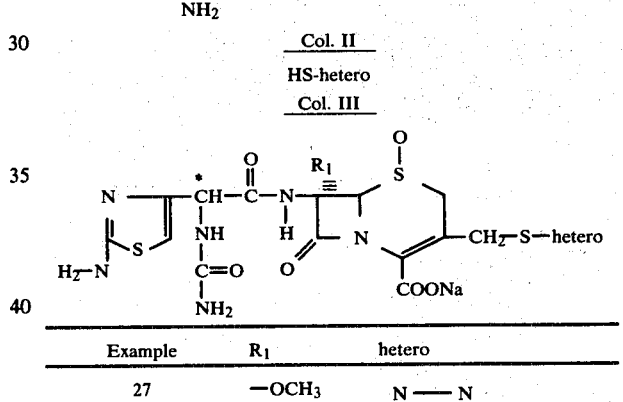

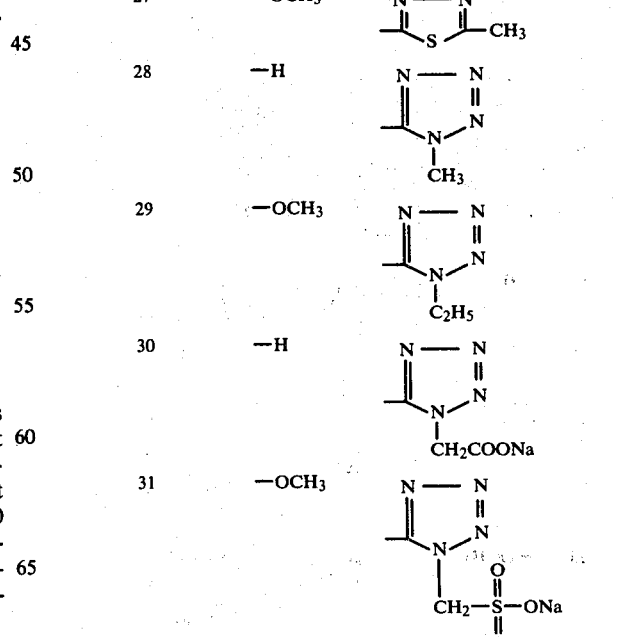

| Example | $R_1$ | hetero |
|---|---|---|
| 27 | —OCH$_3$ | N—N, S, CH$_3$ |
| 28 | —H | N—N, N—N, CH$_3$ |
| 29 | —OCH$_3$ | N—N, N—N, C$_2$H$_5$ |
| 30 | —H | N—N, N—N, CH$_2$COONa |
| 31 | —OCH$_3$ | N—N, N—N, CH$_2$—S(O)$_2$—ONa |

-continued

| 32 | —H | 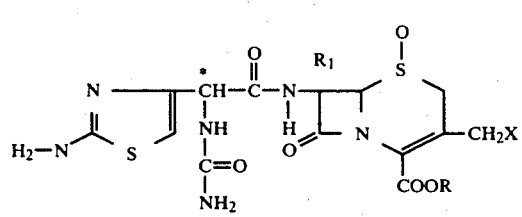 |
| 33 | —H | 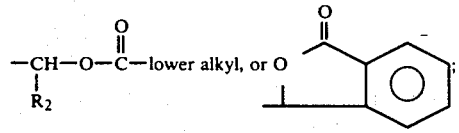 |
| 34 | —H | 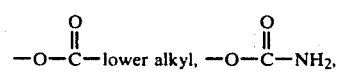 |

The final products of Examples 27-34 are obtained in the D-, L- or D,L-isomeric form depending upon the isomeric form of the cephalosporin shown in Col. I.

The configuration of the sulfoxide group in the products of Examples 27 to 34 depends upon the configuration of the sulfoxide starting material shown in Col. I.

What is claimed is:

1. A compound of the formula

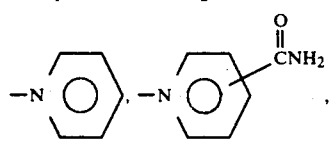

including the imino tautomer form wherein

R is hydrogen, sodium, potassium, t-butyl, benzyl, p-methoxybenzyl, p-nitrobenzyl, diphenylmethyl, 2,2,2-trichloroethyl, trimethylsilyl, —CH$_2$—O-lower alkyl,

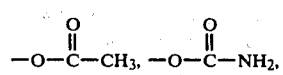

R$_1$ is in the α-configuration and is hydrogen or methoxy;

R$_2$ is hydrogen or lower alkyl;

X is hydrogen,

—O—C(=O)—lower alkyl, —O—C(=O)—NH$_2$,

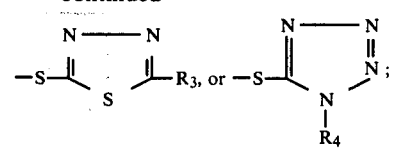

R$_3$ is hydrogen or lower alkyl;

R$_4$ is hydrogen, lower alkyl,

—(CH$_2$)$_n$—C(=O)—OR$_5$, —(CH$_2$)$_n$—S(=O)$_2$—OR$_5$, or —(CH$_2$)$_n$—N—(lower alkyl)$_2$;

R$_5$ is hydrogen, sodium or potassium; and n is an integer from 1 to 4.

2. The compound of claim 1 wherein R is hydrogen, sodium or potassium; R$_1$ is hydrogen; X is hydrogen,

—O—C(=O)—CH$_3$, —O—C(=O)—NH$_2$,

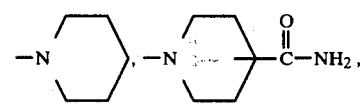

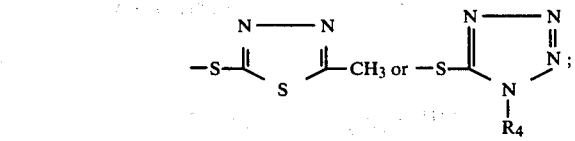

R$_4$ is hydrogen, methyl, —CH$_2$—COOR$_5$,

—CH$_2$—S(=O)$_2$—OR$_5$ or —(CH$_2$)$_2$—N(CH$_3$)$_2$; and R$_5$ is hydrogen, sodium or potassium.

3. The compound of claim 2 wherein the sulfoxide

is in the β-configuration.

4. The compound of claim 3 wherein X is hydrogen.

5. The compound of claim 3 wherein X is

6. The compound of claim 5, [5S-[5α,6β,7α(±)]]-3-[-(acetyloxy)methyl]-7-[[[(aminocarbonyl)amino](2-amino-4-thiazolyl)acetyl]amino]-8-oxo-5-thia-1-azabicyclo[4.2.0]oct-2-ene-2-carboxylic acid, 5-oxide.

7. The sodium salt of the compound of claim 6.

8. The compound of claim 3 wherein X is

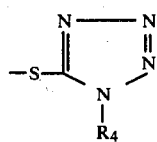

and R₄ is hydrogen, methyl, —CH₂—COOR₅, —CH₂SO₃R₅ or —(CH₂)₂—N(CH₃)₂.

9. The compound of claim 8 wherein X is

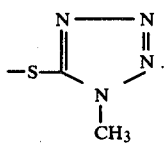

10. The compound of claim 9, [5S-[5α,-6β,7α(±)]]-7-[[[(aminocarbonyl)amino]-(2-amino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide.

11. The sodium salt of the compound of claim 10.

12. The compound of claim 3 wherein X is

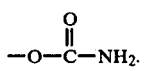

13. The compound of claim 3 wherein X is

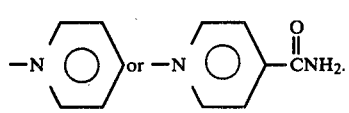

14. The compound of claim 3 wherein X is

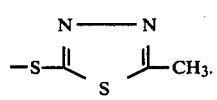

15. An antibacterial pharmaceutical composition comprising a pharmaceutically acceptable carrier and one or more antibacterially active compounds of the formula

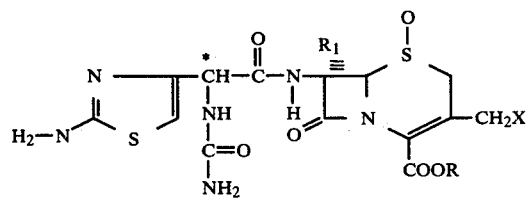

wherein R is hydrogen, sodium, potassium, —CH₂—O—lower alkyl,

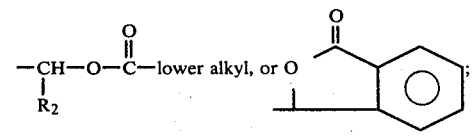

$R_1$ is in the α-configuration and is hydrogen or methoxy; $R_2$ is hydrogen or lower alkyl; X is hydrogen,

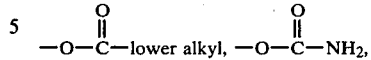

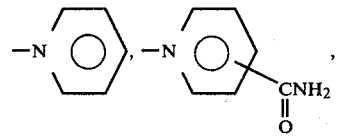

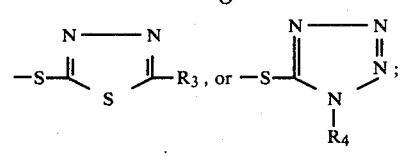

$R_3$ is hydrogen or lower alkyl; $R_4$ is hydrogen, lower alkyl,

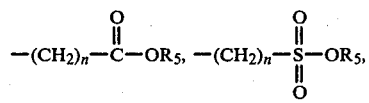

or —(CH₂)ₙN(lower alkyl)₂; $R_5$ is hydrogen, sodium or potassium; and n is an integer from 1 to 4.

16. The composition of claim 15 wherein R is hydrogen, sodium, or potassium; $R_1$ is hydrogen; X is hydrogen,

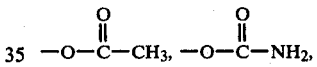

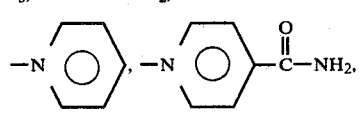

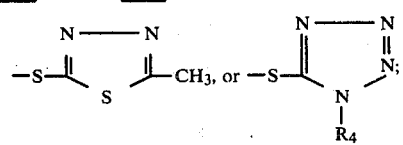

$R_4$ is hydrogen, methyl,

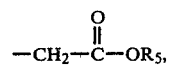

—CH₂—SO₃R₅, or —(CH₂)₂—N(CH₃)₂; and $R_5$ is hydrogen, sodium or potassium.

17. The composition of claim 16 wherein the sulfoxide

is the the β-configuration.

18. The composition of claim 17 wherein X is

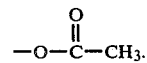

19. The composition of claim 17 wherein

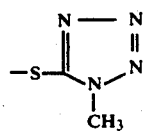
20. The method of treating a bacterial infection in a mammal which comprises parenterally administering an antibacterially effective amount of the composition of claim 15.
* * * * *

UNITED STATES PATENT AND TRADEMARK OFFICE
CERTIFICATE OF CORRECTION

PATENT NO. : 4,275,062    Page 1 of 2

DATED : June 23, 1981

INVENTOR(S) : Hermann Breuer, et al.

It is certified that error appears in the above-identified patent and that said Letters Patent are hereby corrected as shown below:

Col. 3, line 3 in the structure, underline "$R_1$" with three parallel horizontal lines.

Col. 6, line 61, there should be an asterisk above the "C".

Col. 9, line 46, "diphenylmethylester" should read -- diphenylmethyl ester --.

Col. 10, line 7, "5-oxidediphenylmethyl" should read -- 5-oxide diphenylmethyl--.

Col. 10, line 33, "[5S-[5α,6β,7α(35)]]" should read -- [5S-[5α,6β,7α($\pm$)]] --.

Col. 13, Example 11 under sub-heading R, "-CH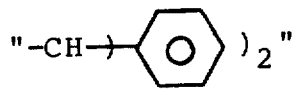)$_2$" should read -- -CH)$_2$ --.

Col. 15, line 10 in the structure, underline "$R_1$" with three parallel horizontal lines.

Col. 15, line 25, in the structure, underline "$R_1$" with three parallel horizontal lines.

UNITED STATES PATENT AND TRADEMARK OFFICE
CERTIFICATE OF CORRECTION

PATENT NO. : 4,275,062

DATED : June 23, 1981

INVENTOR(S) : Hermann Breuer, et al.

It is certified that error appears in the above-identified patent and that said Letters Patent are hereby corrected as shown below:

Col. 17, in the structure of Claim 1 at line 34, underline "$R_1$" with three parallel horizontal lines.

Col. 18, in Claim 2, " 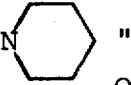 " should read --  --.

Col. 18 in Claim 2, "  " should read

-- 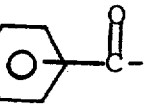 --.

Signed and Sealed this

Twenty-seventh Day of October 1981

[SEAL]

Attest:

Attesting Officer

GERALD J. MOSSINGHOFF

Commissioner of Patents and Trademarks